（12) United States Patent
Howlett et al.

(10) Patent No.: US 6,955,258 B2
(45) Date of Patent: Oct. 18, 2005

(54) DENTAL IMPLANT PACKAGING SYSTEM

(75) Inventors: Charles W. Howlett, Laguna Beach, CA (US); Grant Bullis, Corona, CA (US); Angel Bernardo, Fountain Valley, CA (US)

(73) Assignee: Nobel Biocare AB, Gothenburg (SE)

( * ) Notice: Subject to any disclaimer, the term of this patent is extended or adjusted under 35 U.S.C. 154(b) by 167 days.

(21) Appl. No.: 10/632,127

(22) Filed: Jul. 31, 2003

(65) Prior Publication Data

US 2005/0023166 A1 Feb. 3, 2005

(51) Int. Cl.[7] .............................................. A61B 19/02
(52) U.S. Cl. ...................... 206/63.5; 206/368; 433/173
(58) Field of Search ............................... 206/63.5, 339, 206/368, 369, 521; 433/141, 167, 173, 174

(56) References Cited

U.S. PATENT DOCUMENTS

| 2,347,567 A | 4/1944 | Kresse |
|---|---|---|
| 3,346,135 A | 10/1967 | Haitsch |
| 3,481,712 A | 12/1969 | Bernstein et al. |
| 4,158,256 A | 6/1979 | Wiland et al. |
| 4,187,609 A | 2/1980 | Edelman |
| 4,465,463 A | 8/1984 | Hison Olde |
| 4,553,942 A | 11/1985 | Sutter |
| 4,600,388 A | 7/1986 | Linkow |
| 4,722,688 A | 2/1988 | Lonca |
| 4,856,648 A | 8/1989 | Krueger |
| 4,856,994 A | 8/1989 | Lazzara et al. |
| 4,955,811 A | 9/1990 | Lazzara et al. |
| 5,013,242 A | 5/1991 | Prezmecky |
| 5,030,096 A | 7/1991 | Hurson et al. |
| 5,062,800 A | 11/1991 | Niznick |
| 5,100,323 A | 3/1992 | Friedman et al. |
| 5,105,690 A | 4/1992 | Lazzara et al. |
| 5,108,288 A | 4/1992 | Perry |
| 5,158,458 A | 10/1992 | Perry |
| 5,213,500 A | 5/1993 | Salazar et al. |
| 5,254,005 A | 10/1993 | Zuest |
| 5,290,171 A | 3/1994 | Daftary et al. |
| 5,297,561 A | 3/1994 | Hulon |
| 5,302,125 A | 4/1994 | Kownacki et al. |
| 5,306,309 A | 4/1994 | Wagner et al. |
| 5,312,254 A | 5/1994 | Rosenlicht |
| 5,322,443 A | 6/1994 | Beaty |
| 5,338,196 A | 8/1994 | Beaty et al. |
| 5,368,160 A | 11/1994 | Leuschen et al. |
| 5,368,483 A | 11/1994 | Sutter et al. |
| 5,417,570 A | 5/1995 | Zuest et al. |
| 5,433,330 A | 7/1995 | Yatsko et al. |
| 5,437,550 A | 8/1995 | Beaty et al. |
| 5,453,010 A | 9/1995 | Klein |

(Continued)

FOREIGN PATENT DOCUMENTS

DE 9014729.4 1/1991

(Continued)

*Primary Examiner*—Luan K. Bui
(74) *Attorney, Agent, or Firm*—Knobbe, Martens, Olson & Bear, LLP.

(57) ABSTRACT

Disclosed is a device and method for use in the dental implant industry. Generally, the device relates to packaging systems for dental implants that are capable of storing implants of different lengths and varying diameters. An embodiment of the package may be composed of a vial for housing a cushion. Located on the cushion is a sleeve for housing at least a portion of a dental implant. The sleeve and implant are covered by a sleeve cap whereby the sleeve cap is constructed to hold a healing screw. The packaging system also includes a lid for covering the healing screw.

19 Claims, 4 Drawing Sheets

U.S. PATENT DOCUMENTS

| | | |
|---|---|---|
| 5,462,436 A | 10/1995 | Beaty |
| 5,507,463 A | 4/1996 | Kobylinski et al. |
| 5,525,314 A | 6/1996 | Hurson |
| 5,538,428 A | 7/1996 | Staubli |
| 5,558,230 A | 9/1996 | Fischer et al. |
| 5,564,924 A | 10/1996 | Kwan |
| 5,569,037 A | 10/1996 | Moy et al. |
| 5,582,299 A | 12/1996 | Lazzara et al. |
| 5,622,500 A | 4/1997 | Niznick |
| 5,636,991 A | 6/1997 | Mays |
| 5,651,675 A | 7/1997 | Singer |
| 5,683,464 A | 11/1997 | Wagner et al. |
| 5,692,904 A | 12/1997 | Beaty et al. |
| 5,733,124 A | 3/1998 | Kwan |
| 5,755,575 A | 5/1998 | Biggs |
| 5,887,707 A | 3/1999 | Anascavage et al. |
| 5,904,483 A | 5/1999 | Wade |
| 5,961,330 A | 10/1999 | Hanson |
| 5,964,591 A | 10/1999 | Beaty et al. |
| 5,967,305 A | 10/1999 | Blonder et al. |
| 5,979,643 A | 11/1999 | Blonder et al. |
| 5,996,779 A | 12/1999 | Klardie et al. |
| 6,217,332 B1 * | 4/2001 | Kumar ............... 206/368 |
| 6,247,932 B1 | 6/2001 | Sutter |
| 6,247,933 B1 | 6/2001 | Wagner et al. |
| 2004/0043358 A1 * | 3/2004 | Howlett et al. ......... 433/173 |

FOREIGN PATENT DOCUMENTS

| | | |
|---|---|---|
| EP | 0 630 621 A1 | 12/1994 |
| WO | WO 96/25895 | 6/1996 |
| WO | WO 97/20518 | 6/1997 |
| WO | WO 98/53755 | 5/1998 |
| WO | WO 98/52490 | 11/1998 |
| WO | WO 98/53755 | 12/1998 |

* cited by examiner

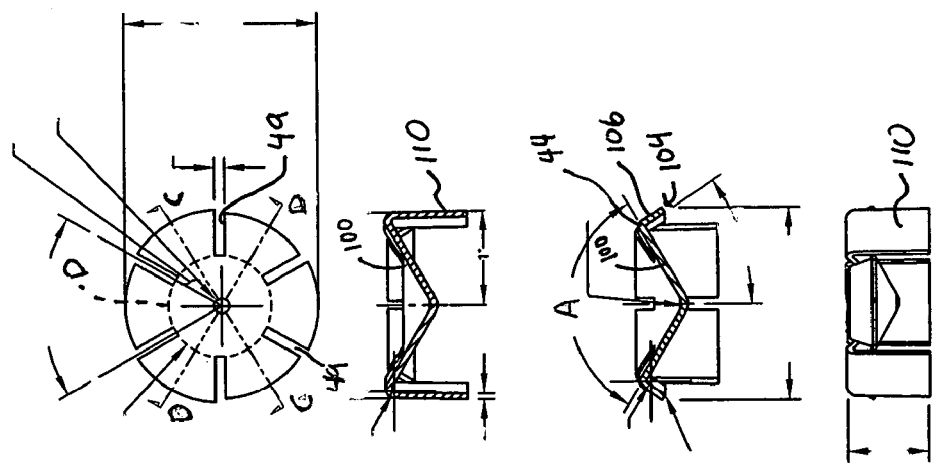

DENTAL IMPLANT PACKAGING SYSTEM

BACKGROUND OF THE INVENTION

1. Field of the Invention

This invention relates to packaging systems and, in particular, to packaging systems for dental implants.

2. Description of the Related Art

Dental implants are placed in the jaw to provide support for a dental restoration, fixed bridge or removable partial denture. Dental implants provide good chewing function and also improve the patient's cosmetic appearance thereby allowing the patient to smile, speak, and interact with others with greater confidence.

One type of dental implant widely used in the industry is typically referred to as a "threaded" implant. Threaded implants have an externally threaded body portion which is screwed into a pre-drilled hole (i.e. an osteotomy) in the patient's upper or lower jawbone. Typically, the threaded implant body is formed with a central threaded socket accessible through the overlying gum tissue for receiving and supporting one or more dental attachments or components. Types of attachments and components that are received by the central socket include healing caps, impression copings and abutments. In turn, some of these attachments and components are useful to fabricate and/or support the prosthodontic restoration.

Dental implants are typically packaged as an assembly including all the tools necessary for the insertion of the implant into an osteotomy formed in the jaw. A typical threaded implant assembly may include a threaded implant body, an implant carrier, an insertion post, a coupling screw and a healing cap. Conventionally, these components are sterilized, pre-assembled and packaged in a sterile vial. The implant carrier, insertion post, and coupling screw are tools which are used during the insertion of the implant body. Typically, the implant carrier, insertion post, coupling screw and vial are discarded after the implant body has been inserted into the osteotomy. The healing cap seals and protects the central socket of the implant body during the initial healing period, and then is discarded.

During the insertion of a conventional threaded implant, the insertion post is mechanically coupled to the top of the implant body by a coupling screw which traverses a central through-cavity in the insertion post and is threaded into the central threaded socket in the implant body. Typically, the bottom end of the insertion post is formed with a hexagonal cavity that irrotationally mates with a corresponding hexagonal protrusion formed on the top of the implant body thereby preventing any relative rotation between the insertion post and implant body while coupled.

An implant carrier is releasably coupled to the top of the insertion post and provides the dental practitioner with a means to grip and manipulate the assembly during the initial implantation procedure. Typically, the implant carrier is formed with a generally hexagonal internal passage at its bottom end which mates with a generally hexagonal outer surface near the top of the insertion post. The dental practitioner uses the implant carrier to manipulate the implant body into the proper location within the jawbone. Torque is applied to the implant carrier which is transferred, via the insertion post, to the threaded implant body.

In use, the first step of a typical implantation procedure involves making an incision in the patient's gum tissue. A portion of the gum tissue is then folded back and an osteotomy is drilled in the jawbone. The diameter of the osteotomy is equal to or slightly smaller than the diameter of the implant body. The implant carrier is then used to transport the threaded implant assembly to the surgical site. The implant carrier is gripped by the practitioner and is used to manipulate the implant body into the correct position and then to partially screw the threaded implant body into the osteotomy.

Once the implant body has been initially placed in the osteotomy and tightened manually, the implant carrier is decoupled from the insertion post and is removed from the surgical site. If necessary, a suitable wrench or dental hand piece is then used to engage the insertion post and drive the implant to its final depth within the osteotomy. The coupling screw is then removed and the insertion post is decoupled from the implant body leaving only the implant body in the patient's mouth.

The healing cap is housed in a cavity formed in the top of the implant carrier where it is contained by a paper barrier until needed. At this point, the healing cap is removed from the implant carrier and is threaded into the central socket of the implant body. Typically, a tool with a hexagonal tip is inserted into a corresponding mating hexagonal recess located in the top center of the healing cap and is used to apply torque to tighten the healing cap. The healing cap protects the implant socket against bone or tissue ingrowth during the initial healing period, and also prevents the entry of bacteria or other contaminants into the central socket of the implant body.

The insertion of the implant body and healing cap is then followed by an initial healing period in which the bone is allowed to surround and retain the implant (i.e. "osseointegrate" with the implant) and the gum tissue is allowed to heal over the implant body and healing cap. For implants placed in the mandible, healing typically requires about three months; for implants in the maxilla, the healing period typically requires about six months.

After the implant body has sufficiently osseointegrated with the jawbone, the gum tissue is re-opened by making an incision and the gum tissue is folded back to expose the healing cap. A hexagonal tool is inserted into the recess in the top of the healing cap and torque is applied to rotate the healing cap out of the implant socket and to remove it from the implant body. During this step of the procedure, great care must be used to remove the healing cap without disturbing the position of the implant body. Any disturbance of the implant body during the removal of the healing cap could damage the osseointegration between the implant body and the jawbone. Damage to the osseointegration is very undesirable and could endanger the entire restoration process by destabilizing the implant. In addition, any movement of the implant body could result in gaps or spaces between the implant body and jawbone which could in turn lead to infection by bacteria and/or other contaminants.

After the healing cap has been unscrewed and removed from the patient's mouth, a suitable healing abutment is inserted into the central socket. The healing abutment extends through the gum tissue overlying the implant site. A second healing period then ensues in which the gum tissue is allowed to heal around the post-osseointegration healing abutment. Typically, this second healing period lasts from four to eight weeks.

After the second healing period has ended, the healing abutment is removed from the implant body. Typically, an impression is taken of the patient's mouth to fabricate a prosthesis or dental restoration. An abutment supporting the final restoration is then attached to the implant body. Lastly, the restoration is cemented or screwed to the abutment and/or implant body to complete the placement of the prosthodontic restoration in the patient's mouth.

The procedure described above for installing a threaded dental implant is commonly used by dental practitioners. However, this procedure suffers from several significant shortcomings. For example, the dental practitioner may choose to attach a wrench or dental hand piece to the threaded implant assembly before transporting the assembly to the surgical site. The dental practitioner may choose to modify the procedure in this manner because it can be difficult to attach the wrench or dental hand piece to the implant assembly inside the patient's mouth. This modification requires the dental practitioner to remove the implant carrier from the implant assembly by gripping the implant assembly with one hand and pulling the implant carrier away from the implant assembly with the other hand. Typically, the wrench or dental hand piece is then attached to the implant assembly by griping the implant assembly with one hand while pushing the wrench or hand piece towards the dental assembly with the other hand. This procedure is undesirable for several reasons. For example, touching the implant assembly can damage and/or contaminate the assembly. This procedure also requires the additional step of removing the implant carrier from the implant assembly.

In addition, to accommodate a range of anatomies and applications, dental implants come in wide variety of diameters and lengths. Accordingly, the corresponding packaging systems must be individually tailored to specifically house implants of predetermined dimensions.

Thus, there exists a need for an improved delivery system for dental implants than has heretofore been available in the prior art.

SUMMARY OF THE INVENTION

Some embodiments of the present invention provide packaging systems that allow storage for dental implants of varying sizes.

Accordingly, one embodiment of the present inventions provides for a packaging device for dental implants that comprises an outer package having top portion and a base portion that are detachably coupled to each other to define a cavity. A sleeve is positioned in the cavity. The sleeve has a side wall extending from a first end and a second end. The first end having a top surface that defines a first opening for receiving a dental implant and the second end defining a second opening. A stop comprises a support surface for supporting the dental implant in the sleeve and at least one lever arm. The at least one lever arm is configured to exert a force against an inner surface of the sleeve so as to support the stop at a fixed vertical location within the sleeve.

Another embodiment of the present invention provides for Accordingly, one embodiment of the present inventions provides for a packaging device for dental implants that comprises an outer package having top portion and a base portion that are detachably coupled to each other to define a cavity. A sleeve is positioned in the cavity. The sleeve has a side wall extending from a first end and a second end. The first end having a top surface that defines a first opening for receiving a dental implant and the second end defining a second opening. A stop comprises a support surface for supporting the dental implant in the sleeve and means for securing the stop at a fixed vertical position within the sleeve such that the force required to position the stop at the fixed vertical location is less than the force required to remove the stop from the fixed vertical position.

BRIEF DESCRIPTION OF THE DRAWINGS

FIG. 4B is a top view of the stop of FIG. 4A.

FIG. 4C is a cross-sectional view taken through line C—C of FIG. 4B.

FIG. 4D is a cross-sectional view taken through line D—D of FIG. 4B

FIG. 4E is a side elevational view of the stop of FIG. 4A.

DETAILED DESCRIPTION OF THE PREFERRED EMBODIMENTS

As technological advances are made in dental implant technology, there is an increased need on predictable and accurate equipment for used in implant procedures. As described above, dental implant procedures involve surgical incisions wherein artificial devices are inserted into the gumline. Consequently, sterility of the environment and the implant often affect the success of the procedure. As will be explained below, the dental implant packaging systems described above may aid in maintaining a sterile implant. In addition, these embodiments may enable manufacturers of these packages to produce packaging systems that can accommodate varying implant sizes with very few modifications.

Figure 1:
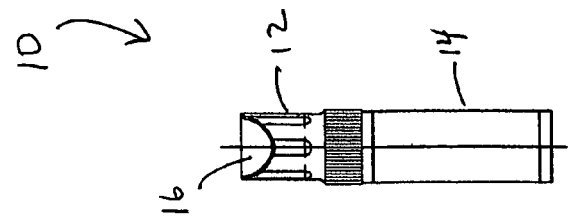
FIG. 1 is a side view of an exemplary embodiment of a dental implant packaging system.

FIG. 1 is a side view of an exemplary embodiment of an implant 38 packaging system. The exemplary embodiment includes an outer vial 10 that comprises a cover 12 and a base 14. The base 14 defines a generally cylindrical cavity and comprises a generally cylindrical side wall that extends between an upper open end 30 and generally horizontal base 14. In a similar manner, the cover 12 defines an upper cavity and comprises a generally cylindrical side wall, a lower open end 18 and a top wall 16 which closes the top end of the cover 12. However, those of skill in the art will recognize that the shape of the outer vial 10 may be modified. For example, in one modified embodiment, the outer vial 10 may have a non-circular cross sectional shape (e.g., square).

The cover 12 and the base 14 are preferably detachably coupled to each other. In the illustrated embodiment, the base 14 is provided with threads 32 near the upper open end 16 that are configured to interact with threads (not shown) provided on the lower end 18 of the cover 12. In this manner, the cover 12 may be twisted on and off of the top of base 30 to close the cavity. The cover 12 preferably includes knurling to enhance the user's grip.

In one embodiment, the outer vial 10 is made out of plastic or polystyrene that may be gamma sterilizable. It is anticipated that in modified embodiments the outer vial 10 may be replaced with, for example, shrink wrapping.

Figure 2:
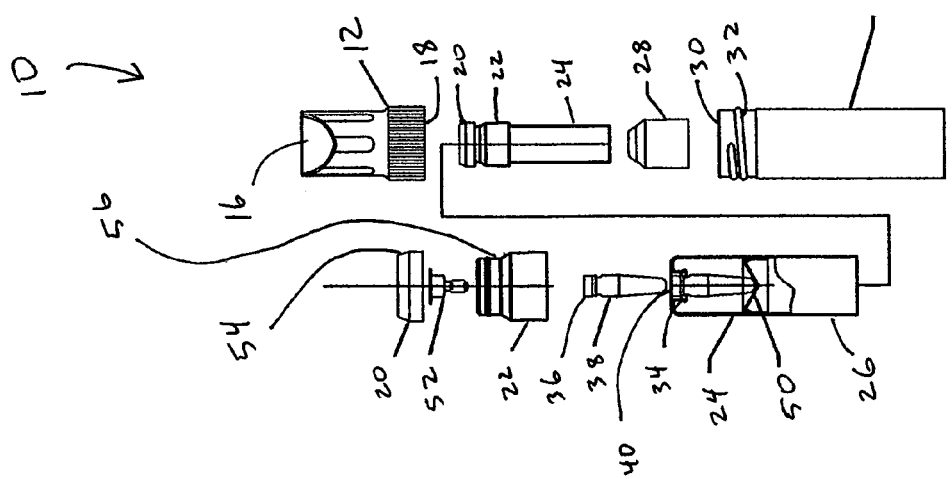
FIG. 2 is an exploded view of the packaging system of FIG. 1.

FIG. 2 is an exploded view of the packaging system of FIG. 1. As shown, the packaging system includes an sleeve combination 20, 22, 24 and a cushion 28, which are positioned within the outer vial 10. As will be explained in more detail below, the sleeve combination 20, 22, 24 comprises a sleeve 24, a sleeve cap 22 and a lid 20. In modified embodiments, more than one sleeve combination 20, 22, 24 and/or cushion 28 may be placed within the vial 10.

The cushion 28 is configured to support the sleeve combination 20, 22, 24 within the base 14 of the outer vial 10. In the exemplary embodiment, the cushion 28 comprises a generally cylindrical body with a top surface configured to support the sleeve combination 20, 22, 24 and a lower surface configured to rest within the lower cavity on the base 14 of the lower portion of the vial. In one embodiment, the cushion 28 is made from a thermoplastic elastomer.

In the exemplary embodiment, the cushion 28 is configured to dampen vibrations and protect the contents of the sleeve combination 20, 22, 24 from damage caused by such vibrations. In addition, the cushion 28 may be used to properly center and position the sleeve combination 20, 22, 24 within the lower portion of the vial. For example, the sleeve 24 includes a bottom opening 40 that is configured such that it extends over top surface of the cushion 28 such that the sleeve 24 is maintained in a centralized position within the vial. The sleeve 24 and cushion 28 arrangement may alternatively be configured such that the sleeve 24 fits within a recessed portion of the cushion 28 such that the sleeve 24 is also maintained in a central portion of the vial. However, it is understood that other embodiments of the packaging system may not include a cushion 28 and/or may include a spacer positioned within the lower portion.

Figure 3:
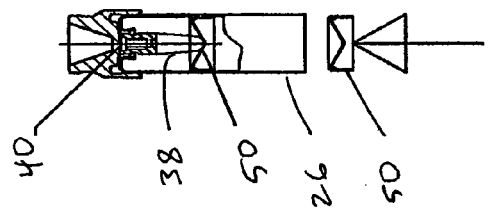
FIG. 3 is a cross-sectional view of the packaging system of FIG. 1.
Figure 4A:
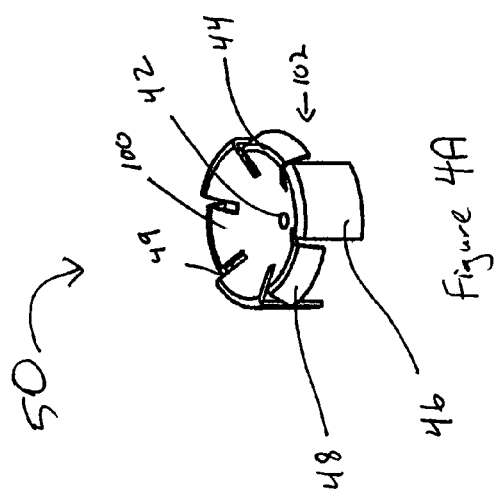
FIG. 4A is a perspective view of a stop of the packaging system of FIG. 1.
Figure 5:
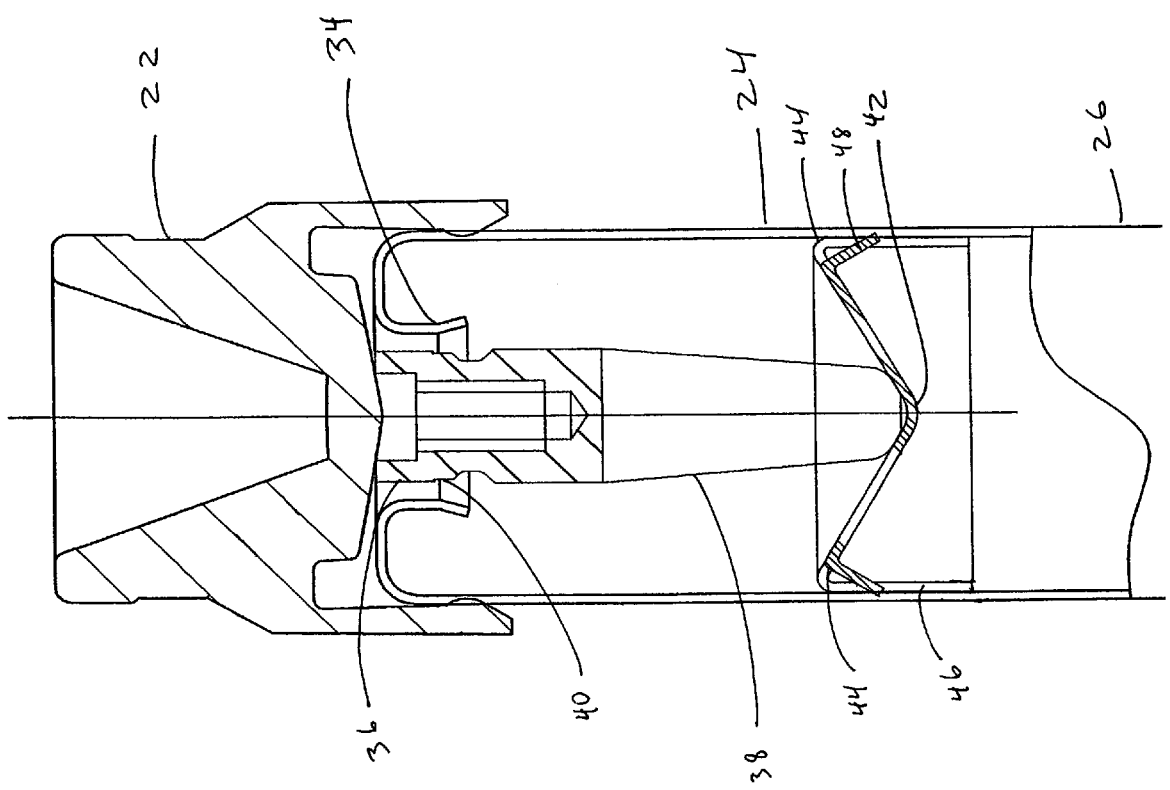
FIG. 5 is an enlarged cross-sectional view of the packaging system of FIG. 1.

With reference to FIGS. 2, 3 and 5, the sleeve 24 comprises a generally cylindrical body that includes a cylindrical side wall and a top surface. As mentioned above, the sleeve 24 may have an open lower end 18. The top surface may also include an opening 40. In the exemplary embodiment, the opening 40 is formed by a downwardly extending annular flange 48, which extends from the top surface of the sleeve 24. In one embodiment, the opening 40 is sized and dimensioned to surround a collar 36 of an implant 38 that is positioned within the packaging system. For implants 38 with a generally circular cross-section, the opening 40 is approximately 0.3 mm–0.5 mm larger than the maximum diameter of the collar of the implant. For example, for a generally circular implant 38 with a diameter of 3.5 millimeters, the opening 40 has an approximately 4.0 millimeter diameter; for an implant diameter of 4.3 millimeters, the opening 40 has a diameter of approximately 4.6 millimeters; for an implant diameter of 5.0 millimeters the opening 40 has a diameter of approximately 5.3 millimeters; and for 6.0 millimeter diameter the opening 40 has a diameter of approximately 6.3 millimeters. It should also be appreciated that the opening 40 can be configured to receive implants 38 with non-circular cross-sections. In such embodiments, the opening 40 may be circular or non-circular. In one such embodiment, the opening 40 is approximately 0.25–0.7 millimeters wider than the largest cross-sectional diameter of the collar 36 of the implant 38.

It should be appreciated that although the sleeve 24 of the present embodiment is tubular, the sleeve 24 may be constructed of a variety of other shapes. In one embodiment, the sleeve 24 is formed of a metal, preferably titanium. However, it is understood that a variety of materials and metals may be used for construction of the sleeve 24, such as, for example, plastics, thermoplastics, steel, iron, titanium, aluminum and nickel. The sleeve 24 may also be an assembly of the same or dissimilar materials.

As will be explained in more detail below, it is generally desirable that the top surface of the implant 38 is located near the top surface of the sleeve 24. In one embodiment, the top surface of the implant 38 lies approximately flush with the top surface of the sleeve 24. In other embodiments, the top surface of the implant 38 may lie approximately 0.35–0.55 mm above or below the top surface of the sleeve 24. It is also generally desirable that the sleeve 24 only contact the collar 36 of the implant 38, which is typically more rugged and thus less easily damaged as compared to the lower portions of the implant 38. Therefore, in the illustrated embodiment, the annular flange 48 only contacts the collar 36 of the implant 38.

As mentioned above, the implant 38 to be stored in the packaging system may be of varying diameters and lengths. To accommodate the various lengths of the implants 38, the sleeve 24 preferable includes a stop 50 for supporting the lower surface of the implant 38 such that the top surface of the implant 38 is positioned near the top surface of the sleeve 24 and opening 40 as described above. The stop 50 is preferably configured such that it can be inserted into the sleeve 24 and positioned at different heights with respect to the top surface of the sleeve 24. In this manner, the stop 50 may be used to positioned different lengths of implants 38 within the vial.

In one preferred embodiment, the force required to insert the stop 50 into the sleeve 24 is substantially lower than the force required to removal the stop 50 once it is positioned in the sleeve 24. In addition, once in place, the stop 50 preferably provide sufficient retention force to support the implant 38 within the sleeve 24. In one embodiment, the insertion force is approximately 10%–15% of the removal force. In such an embodiment, the force required to push the stop 50 out of the sleeve 24 once it is positioned may be greater than approximately 10 lbs (44.5 N) and the insertion force may be approximately 1–2 lbs. (4.45–8.9 N). As will be explained in more detail below, the stop 50 preferably includes retention structures, which provide the function described above.

With particular reference to FIGS. 4A–E, the stop 50 of the exemplary embodiment comprises a support surface 100 and one or more generally downwardly extending flanges 102, which, as will be explained below, form in part the retention structures. In the illustrated embodiment, the surface 100 has a generally conical shape and extends from an outer edge 44 to an apex or pointed center 42 which is positioned generally at the center of the stop 50 below the outer edge 44. As seen in FIG. 5, the apex 42 provides a seat for the typically rounded lower end 18 of the implant 38. The apex also helps to center the implant 38 within the opening 40 of the sleeve 24. In one preferred embodiment, the surface 100 has a conical angle A of approximately 120 degrees (see FIG. 4D).

Some of the flanges 102 define in part lever arms 48. In the illustrated embodiment, the lever arms 48 are defined between radially extending slots 49 that extend from the distal end 104 of a downwardly extending segment 106 into the top surface 100. In one embodiment, the slots 49 are approximately 0.63–0.47 mm wide, in another embodiment the slots 49 are approximately 0.5 mm wide. In such embodiments, the slots 49 may extend from the distal end to an imaginary circle D (see FIG. 4B) that has a diameter approximately 5.13–4.87 mm around the center of the top surface 100. In other embodiments, the slots 49 may extend approximately 5 mm from the center. The lever arms 48 extend downwardly from the outer edge 44 of the top surface. The lever arms 48 extends at an angle that is not perpendicular to the longitudinal axis of the vial. Preferably, in a natural or relaxed state, the distal end of the lever arms 48 would extend slightly beyond the inner diameter of the sleeve 24. In one embodiment, in the relaxed state, there is approximately a 0.25 mm interference between the lever arms 48 and the inside of the sleeve 24 and the lever arms 48 are formed at approximately a 30° angle with respect to the vertical walls of the sleeve 24. In this manner, as the stop 50 is inserted into the sleeve 24, the lever arms 48 are flexed inwardly as the arms 48 bend about the apex 42 and the outer edge 44. Because the stop 50 is formed in such a way that the arms 48 flex, the lever arm 48 exerts an outward force against the sleeve 24 to support stop 50 at a specific height within the sleeve 24. Preferably, the lever arms 48 are configured to allow the stop 50 to be press fitted into the sleeve 24 and positioned at specific height with respect to the opening 40.

The stop 50 may be formed from a metallic material, such as, for example, titanium. In one preferred embodiment, the stop 50 is formed from an approximately 0.3 mm thick generally flat sheet of titanium.

In the illustrated embodiment, the flanges 102 also include one or more centering flanges 46, which are positioned between the lever arms 48. The centering flanges 46 comprise a downwardly extending segment 110 which extends from the outer edge 44 of the top surface 100. In one embodiment, the downwardly extending segment 110 preferably has an outer diameter that is approximately 0.10–0.25 millimeters smaller than the inner diameter of the sleeve 24. The downwardly extending centering flanges 46 extend generally parallel to the walls of the sleeve 24 and provide the stop 50 with additional lateral stability. In one embodiment, the centering flanges 46 have a longitudinal length from the outer edge 44 of approximately 4 millimeters.

In the illustrated embodiment, the stop 50 includes three centering flanges 46 and three lever arms 48 that are alternately spaced approximately 60 degrees apart from each other. However, it should be appreciated that in modified embodiments the stop 50 may include more or less lever arms 48 and/or centering flanges 46 that may be arranged in different orders. In other embodiments, the stop 50 may be formed without the centering flanges 46 and/or the centering flanges 46 and the lever arms 48 may be combined. In addition, those of skill in the art will recognize that the removal and insertion forces can be adjusted by adjusting the structure of the stop 50. For example, the removal and insertion forces may be adjusted by providing more or less lever arms, adjusting the width of the gaps, adjusting the thickness of the material, changing materials, adjusting the angle between the lever arm and the vertical side wall of the vial, adjusting the interference between the lever arm and the vial, and/or adjusting the angle of the top surface with respect to the lever arm. It should also be appreciated that modified embodiments may utilize modified structures for providing an outwardly directed force to hold the stop 50 in place. Such embodiments may include various combinations of deflectable tabs, arms, springs and/or ratchet type arrangements that provide for a removal force that is generally greater than the insertion force.

As mentioned above, the stop 50 may be inserted into the sleeve 24 through the sleeve 24 bottom and thereafter placed in a substantially fixed position within the sleeve 24. As will be explained below, the stop 50 works in conjunction with the sleeve cap 22 to hold the implant 38 such that only the collar 36 contacts the sleeve 24.

The illustrated embodiment is particularly advantageous because it relatively simple to manufacture and machine. However, those of skill of the art will recognize that other configurations may be used to retain the stop 50 within the sleeve 24 through fixed or adjustable connections. For example, fixed connections may include connections which hold the stop 50 in the sleeve 24 in a substantially immovable position. The fixed connections may include chemical or physical bonds between the sleeve 24 and the stop 50 which are applied once the stop 50 is properly positioned within the sleeve 24 to support the implant 38. Adjustable connections may include various connections which hold the stop 50 within the sleeve 24 in a substantially fixed position but at the same time allow the location of the stop 50 to be adjusted within the sleeve 24 without requiring the breaking of chemical or physical bonds. For example, in one embodiment of an adjustable connection, the stop 50 is made of a an elastic material that is compressed as it is inserted into the sleeve 24. In another embodiment, the stop 50 and sleeve 24 may be coated with materials to produce sufficient a friction force between the sleeve 24 and the segments of the stop 50. In still other embodiments, the sleeve 24 may be provided with various ridges and/or grooves 56 which provide for a ratchet type motion of the stop 50 with respect to the sleeve 24.

With reference now to FIGS. 2 and 3, the sleeve cap 22 will now be described. In the illustrated embodiment, sleeve cap 22 is preferably located above the sleeve 24 and used for covering the implant 38 to maintain its sterile integrity. The sleeve cap 22 includes a lower portion which includes an outer downwardly extending segment that defines an inner surface. The inner surface has a diameter that is configured such that the sleeve cap 22 can be press-fitted onto the sleeve 24. In one embodiment, the sleeve cap 22 and, in particular, the segment of the sleeve cap 22 is made of a resilient flexible material such as, for example, a thermoplastic elastomer. In this manner, the segment secures the sleeve cap 22 to the sleeve 24.

The lower portion of the sleeve cap 22 preferably includes a centering post. As seen in FIG. 3, when the sleeve cap 22 is positioned on the sleeve 24 the centering post preferably contacts the top surface of the implant 38. In this manner, the implant 38 may be held snugly between centering post and the stop 50 to hold the implant 38 in a centralized location within the sleeve 24. In addition, the centering post is preferably made from a resilient material which provides cushioning to prevent damage to the top surface of the implant 38.

With continued reference to FIGS. 2, 3 and 5, the sleeve cap 22 may include a top portion that is configured for storing a healing screw 52 or cap. In the illustrated embodiment, the sleeve cap 22 comprises a top surface which includes a closed bore that defines a cavity in which the healing screw 52 may be positioned. The top portion includes outer side walls which are configured to detachably receive a lid 20. In the illustrated embodiment, the lid 20 includes an annular ridge 54 which is configured to mate with a lip or groove 56 on the sleeve cap 22. In this manner, the lid 20 may be peeled off of the sleeve cap 22 to expose the healing screw 52. In other embodiments, the lid 20 and the top portion of the cap sleeve 24 may include corresponding threads 32 or other arrangements for providing a detachable connection.

Figure 6:
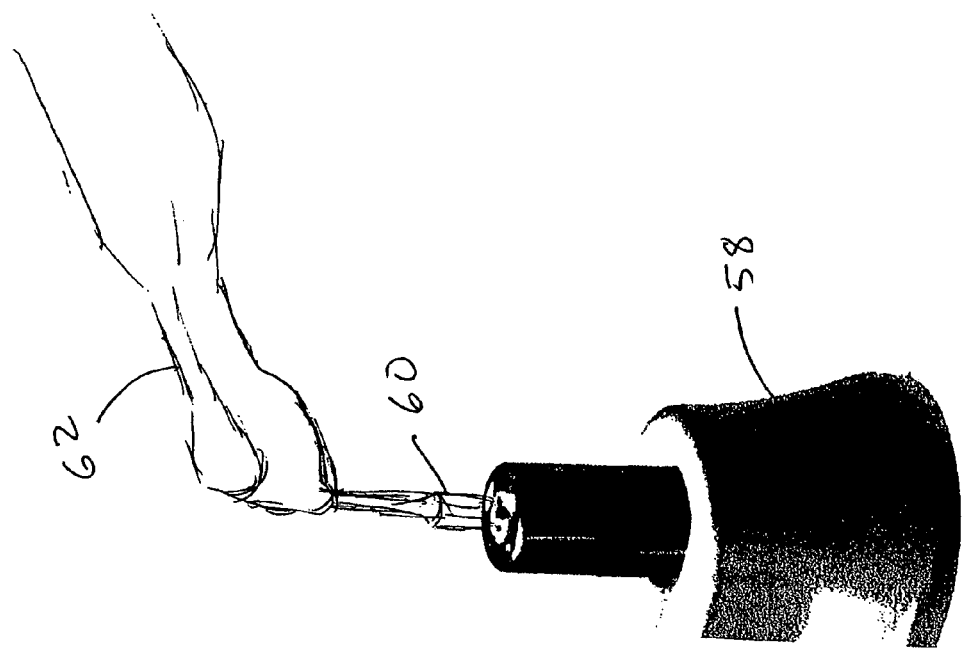
FIG. 6 is a perspective view of a sleeve holder and a sleeve of the packaging system of FIG. 1.

In one embodiment of use, the lid 20 of the outer vial 10 is first removed to expose the sleeve combination 20, 22, 24. The sleeve cap 22 may the be detached from the top of the sleeve 24 to expose the top surface of the implant 38. The sleeve 24 may then be positioned within a sleeve 24 holder (see e.g., FIG. 6) or held. A driver 60 may then be inserted into the implant 38 and the dental implant 38 may be lifted out of the sleeve 24 by using of the driver 60, which may include releasable retention structures (e.g., gripping arms, O-rings, etc.) for coupling the driver 60 to the implant 38.

The handpiece 62 with the driver 60 may then be used to place the dental implant 38 within the jaw of a patient. The lid 20 of the sleeve cap 22 may then be removed to release the healing screw 52. The healing screw 52 may then be attached to the dental implant 38.

The dental implant 38 packaging system described above has several advantages. For example, the stop 50 allows the sleeve 24 to accommodate various lengths of dental implants 38 within a single sleeve 24. In this manner, the number of components are reduced and manufacturing costs can be decreased. In other embodiments, dental implants 38 may be formed in a fixed number of diameters with each diameter having a different length. To accommodate such a set of implants 38, for each diameter of implant 38 a standard sleeve 24 may be manufactured with a standard outer diameter and length. The opening 40 within the sleeve 24 may be varied to accommodate the different diameters of the implants 38. A standard stop 50 may then be configured to fit within each sleeve 24 to support the implant 38 within the sleeve 24. The sleeve combination 20, 22, 24 may then be positioned within a standard outer vial 10. In this manner, various diameters of implants 38 maybe packaged in a packing system that uses common parts for the stop 50, the sleeve cap 22 and the outer vial 10.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combination or subcombinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above.

What is claimed is:

1. A packaging device for dental implants, comprising:
    an outer package having top portion and a base portion that are detachably coupled to each other to define a cavity;
    a sleeve positioned in the cavity, the sleeve having a side wall extending from a first end and a second end, the first end having a top surface that defines a first opening for receiving a dental implant and the second end defining a second opening,
    a stop comprising a support surface for supporting the dental implant in the sleeve and at least one lever arm, the at least one lever arm being configured to exert a force against an inner surface of the sleeve so as to support the stop at a fixed vertical location within the sleeve.

2. The packaging device as in claim 1, wherein the at least one lever arm is configured such that an insertion force required to insert the stop into the sleeve and position the stop at the fixed vertical location is less than a removal force required to remove the stop from the fixed vertical location.

3. The packaging device as in claim 2, wherein the insertion force is less than 15% of the removal force.

4. The packaging device as in claim 2, wherein the insertion force is less than 10% of the removal force.

5. The packaging device as in claim 2, wherein the removal force is greater than about 10 lbs.

6. The packaging device as in claim 1, wherein the at least one lever arm is formed at least in part from a portion of the support surface and a downwardly extending flange that extends from the support surface, the lever arm being defined between a pair of slots that extend through the downwardly extending flange and into the support surface.

7. The packaging device as in claim 6, wherein the downwardly extending flange forms an angle of approximately 30 degrees with respect a longitudinal axis of the sleeve.

8. The packaging device as in claim 1, wherein the support surface is conical.

9. The packaging device as in claim 8, wherein the support surface forms an angle of approximately 120 degrees with respect to a longitudinal axis of the sleeve.

10. The packaging device as in claim 1, wherein the second opening is formed from an annular flanges that extends downwardly from the top surface of the sleeve.

11. The packaging device as in claim 1, wherein the stop includes at least one centering flange which extends from the support surface and is approximately parallel to a longitudinal axis of the sleeve.

12. The packaging device as in claim 11, wherein the stop includes three centering flanges and three lever arms.

13. The packaging device as in claim 1, further comprising a cushion that is positioned in the cavity between the second end of the sleeve and a bottom surface of the base portion.

14. The packaging device as in claim 1, further comprising a cap that includes an annular flange configured to fit around and over the second end of the sleeve, the cap including a centering portion within the annular flange that is configured such that when the cap is coupled the sleeve the implant is secured in a vertical direction between the centering portion and the stop.

15. The packaging system as in claim 14, wherein the cap includes a cavity for receiving a healing cap and a lid for enclosing the healing cap within the cavity.

16. A packaging system, comprising:
    a dental implant having a collar with a first diameter
    an outer package having top portion and a base portion that are detachably coupled to each other to define a cavity;
    a sleeve positioned in the cavity, the sleeve having a side wall extending from a first end and a second end, the first end defining a first opening having a diameter that is larger than the first diameter and the second end defining a second opening,
    a stop that is insertable through the second opening, the stop comprising a first surface for supporting the dental implant in the sleeve, and
    means for securing the stop at a fixed vertical position within the sleeve such that the force required to position the stop at the fixed vertical location is less than the force required to remove the stop from the fixed vertical position.

17. The packaging system as in claim 16, further comprising a cushion that is positioned in the cavity between the second end of the sleeve and a bottom surface of the base portion.

18. The packaging device as in claim 16, further comprising a cap that includes an annular flange configured to fit around and over the second end of the sleeve, the cap including a centering portion within the annular flange that is configured such that when the cap is coupled the sleeve the implant is secured in a vertical direction between the centering portion and the stop.

19. The packaging system as in claim 18, wherein the cap includes a cavity for receiving a healing cap and a lid for enclosing the healing cap within the cavity.

* * * * *